United States Patent
Kelly

(10) Patent No.: US 9,089,704 B2
(45) Date of Patent: *Jul. 28, 2015

(54) OPERATIONAL ELECTRODE IMPEDANCE MEASUREMENT FOR AN IMPLANTABLE MEDICAL STIMULATOR

(71) Applicant: Medtronic, Inc., Minneapolis, MN (US)

(72) Inventor: Kevin J. Kelly, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/839,439

(22) Filed: Mar. 15, 2013

(65) Prior Publication Data
US 2013/0211478 A1   Aug. 15, 2013

Related U.S. Application Data

(63) Continuation of application No. 11/846,142, filed on Aug. 28, 2007, now Pat. No. 8,644,930.

(60) Provisional application No. 60/840,642, filed on Aug. 28, 2006.

(51) Int. Cl.
*H04R 25/00* (2006.01)
*A61N 1/36* (2006.01)
*H04R 11/02* (2006.01)

(52) U.S. Cl.
CPC .......... *A61N 1/36128* (2013.01); *H04R 25/456* (2013.01); *H04R 25/604* (2013.01); *H04R 11/02* (2013.01)

(58) Field of Classification Search
CPC . A61N 1/36128; H04R 25/604; H04R 25/456

USPC .......................................................... 381/328
See application file for complete search history.

(56) References Cited

U.S. PATENT DOCUMENTS

| 4,870,341 A | 9/1989 | Pihl et al. |
| 5,487,755 A | 1/1996 | Snell et al. |
| 5,549,654 A | 8/1996 | Powell |

(Continued)

FOREIGN PATENT DOCUMENTS

| WO | 9819738 A1 | 5/1998 |
| WO | 0143821 A1 | 6/2001 |

(Continued)

OTHER PUBLICATIONS

International Search Report for PCT/US2007/076988.

*Primary Examiner* — Jianchun Qin
(74) *Attorney, Agent, or Firm* — IPLM Group, P.A.

(57) ABSTRACT

Controller, system and method for an implantable medical device having a plurality of electrodes, said implantable device being capable of delivering a therapeutic stimulation to a patient. An electrode interface is operatively coupled between a plurality of electrodes and a control module. The control module uses an electrode interface to obtain a plurality of measurements of impedance values for a plurality of selected pairs of individual ones of the plurality of electrodes. A user interface displays an indicia, indicative of operability of a group of at least one of said plurality of electrodes, based on a comparison of said plurality of measurements to a predetermined range, said indicia being a qualitative representation of operability of said group of at least one of said plurality of electrodes.

22 Claims, 5 Drawing Sheets

(56) References Cited

U.S. PATENT DOCUMENTS

| | | | |
|---|---|---|---|
| 5,713,937 A | 2/1998 | Nappholz et al. | |
| 5,724,985 A | 3/1998 | Snell et al. | |
| 5,755,742 A * | 5/1998 | Schuelke et al. | 607/27 |
| 5,891,179 A | 4/1999 | Er et al. | |
| 6,101,415 A | 8/2000 | Er et al. | |
| 6,308,100 B1 | 10/2001 | Er et al. | |
| 6,374,139 B1 | 4/2002 | Er et al. | |
| 6,721,600 B2 | 4/2004 | Jorgenson et al. | |
| 6,748,274 B2 | 6/2004 | Levine et al. | |
| 6,842,644 B2 | 1/2005 | Anderson et al. | |
| 6,978,171 B2 * | 12/2005 | Goetz et al. | 600/547 |
| 2002/0077669 A1 | 6/2002 | Lindh et al. | |
| 2002/0120307 A1 * | 8/2002 | Jorgenson et al. | 607/27 |
| 2003/0088289 A1 | 5/2003 | Levine et al. | |
| 2003/0114899 A1 | 6/2003 | Woods et al. | |
| 2003/0176899 A1 | 9/2003 | Samuelson et al. | |
| 2004/0082980 A1 | 4/2004 | Mouine et al. | |
| 2004/0098063 A1 | 5/2004 | Goetz | |
| 2004/0143303 A1 | 7/2004 | Sieracki | |
| 2004/0225337 A1 | 11/2004 | Housworth et al. | |
| 2005/0010258 A1 | 1/2005 | Peterson et al. | |
| 2005/0033385 A1 | 2/2005 | Peterson et al. | |
| 2005/0107841 A1 * | 5/2005 | Meadows et al. | 607/43 |
| 2006/0036186 A1 | 2/2006 | Goetz et al. | |

FOREIGN PATENT DOCUMENTS

| | | |
|---|---|---|
| WO | 03077992 A1 | 9/2003 |
| WO | 2005068017 A1 | 7/2005 |
| WO | 2006017277 A2 | 2/2006 |
| WO | WO 2006017277 A3 * | 6/2006 |
| WO | 2007112061 A2 | 10/2007 |
| WO | 2007112061 A3 | 10/2007 |

\* cited by examiner

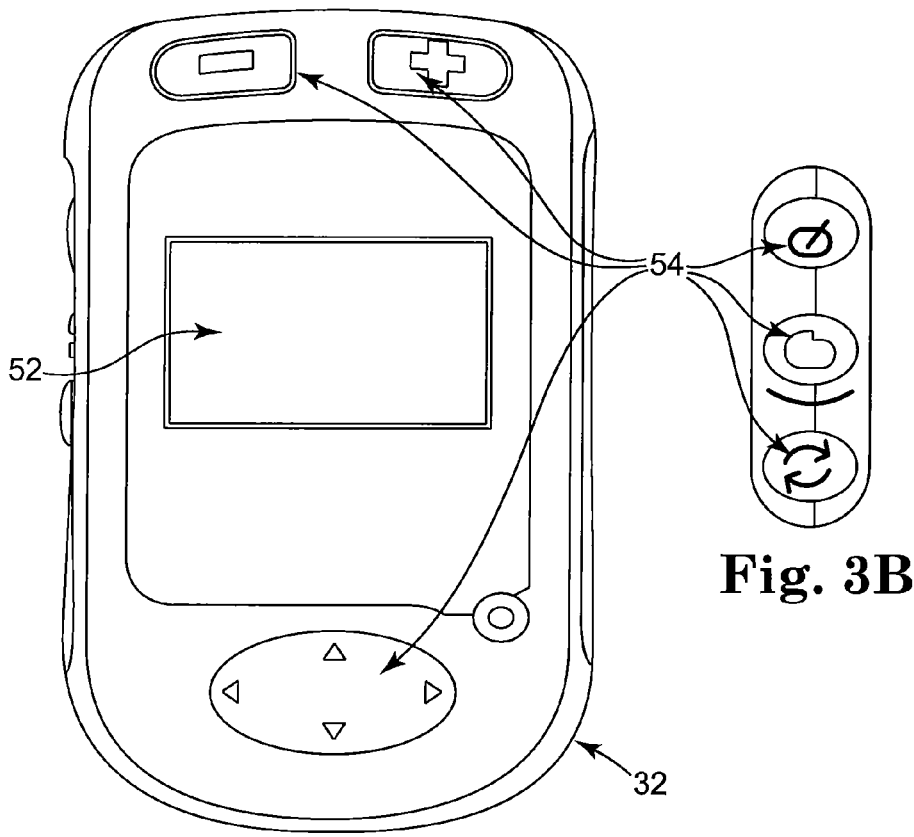
Fig. 3B
Fig. 3A
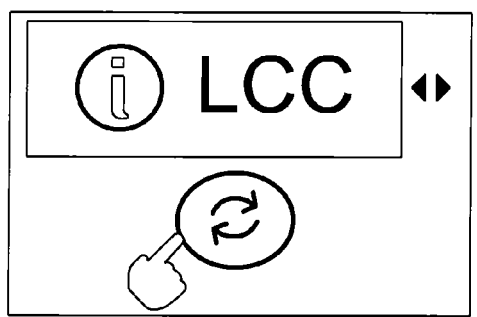
Fig. 3C
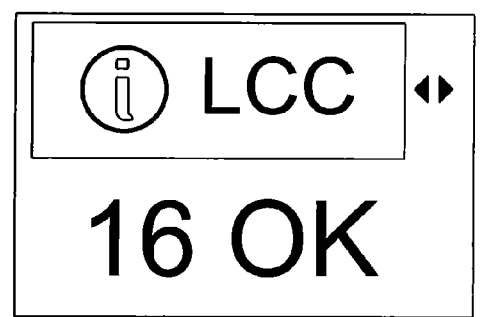
Fig. 3D

OPERATIONAL ELECTRODE IMPEDANCE MEASUREMENT FOR AN IMPLANTABLE MEDICAL STIMULATOR

RELATED APPLICATION

This application is a continuation of U.S. patent application Ser. No. 11/846,142, filed Aug. 28, 2007, which is a non-provisional of provisional U.S. Application Ser. No. 60/840,642, filed Aug. 28, 2006, and claims priority therefrom.

FIELD

The present invention is related generally to implantable medical stimulators and, more particularly, to implantable medical stimulators having electrode impedance measurement capability.

BACKGROUND

The medical device industry produces a wide variety of electronic devices for treating patient medical conditions using electrical stimulation. Depending upon the medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices designed to deliver therapeutic electrical stimulation include neurological stimulators and spinal stimulators as well as pacemakers and defibrillators.

Implantable medical devices configured to deliver therapeutic electrical stimulation commonly deliver therapy via electrodes positioned on one or more leads and operatively connected to the implantable medical device. In some instances, the housing of the implantable medical device may also serve as an electrode or an electrode may be positioned on the housing. The leads and electrodes are commonly positioned in the patient's body during the same surgical procedure in which the implantable medical device is implanted.

The positioning of leads and electrodes is often an inexact procedure and commonly may be dependent on the particular physiologic characteristics of the patient. In addition, leads and electrodes commonly may be positioned within the patient without the medical professional conducting the procedure being capable of actually seeing where the leads are positioned—instead, external aides such as fluoroscopes and endoscopes commonly may be employed to inform the medical professional as to an approximate location of the leads.

Due to the inherent uncertainty involved in the placement of leads and electrodes for an implantable medical device, implantable medical devices and the external controllers that interface with the devices are commonly operable to perform a test on the leads and electrodes to verify that the leads and electrodes are functioning properly and are positioned correctly. A common test is to check the impedance between pairs of electrodes. One electrode will transmit a signal with known electrical characteristics. Another electrode will sense the transmitted signal, and using known, fundamental electrical relationships the differences between the transmitted and sensed electrical signals are used to compute the impedance between the two electrodes. The measured impedance value can give a medical professional information relating to whether the electrodes involved in the test are positioned correctly and working properly.

An external controller, or programmer, is commonly utilized in lead impedance tests. The programmer provides a user interface via a display screen, and is manipulated by a medical professional via a variety of inputs, such as buttons and touchscreens. The programmer commonly communicates with the implantable medical device via inductive telemetry, though communication protocols utilizing far-field radio frequency technology is known in the art. The programmer may communicate with an associated implantable medical device to interface with electrodes connected with the implantable medical device in order to obtain measurements of impedance values of each associated electrode. The values of electrode impedance may then be displayed to a medical professional and a judgment as to the efficacy of each electrode may then be made.

In order to accomplish this, a coil, operatively coupled to the controller, typically by a wire, is placed over a coil operatively coupled to the electronics in the implantable medical device, thereby establishing an inductive telemetry link over which data may be passed in either direction.

For example, U.S. Patent Application Publication No. 2006/0036186, Goetz et al, Automatic Impedance Measurement of an Implantable Medical Device, discloses a method and controller for automating impedance measurements. An entry for each electrode pair is displayed on a user interface. Each electrode pair entry includes an identification of electrodes for an electrode pair, an associated value of impedance, and a value of current that is measured between the electrodes of a pair.

Another example, U.S. Pat. No. 5,891,179, Er et al, Method and Apparatus For Monitoring and Displaying Lead Impedance in Real-Time For an Implantable Medical Device, discloses a method and controller for displaying real-time graphical representations of variable lead impedance. Impedance values are calculated using Ohm's law or other related equations. Then the calculated impedance values are output to a graphic display for presentation thereby in graphical form or are output to a graphic printer, or both.

Another example, U.S. Patent Application Publication No. 2003/0114899, Samuelsson et al, Programming System For Medical Devices, discloses a method and controller for displaying graphical representations of a quantity influenced by the operation of a medical device. Such quantities may include information derived from tests and diagnostics, such as an electrode impedance test.

Another example, U.S. Patent Application Publication No. 2005/0033385, Peterson et al, Implantable Medical Device Programming Apparatus Having a Graphical User Interface, discloses graphical displays of the operation of a medical device, such as a test of a device lead. Results are organized according to the anatomical position of the lead, i.e., whether the lead is an atrial or ventricular lead, allowing the clinician to efficiently assess the functionally of all lead data by virtue of its grouping into precise anatomical categories.

Another example, U.S. Pat. No. 6,721,600, Jorgenson et al, Implantable Lead Functional Status Monitor and Method, discloses a system for obtaining trend data on the status of leads of an implantable medical device. The lead status measurement derives its data from various sources including lead impedance, non-physiologic sensed events, percentage of time the device is in mode switch, the results of capture management operation, sensed events, reversion paced counts, and refractory sense counts. The lead status measurement employs a set of weighted sum rules used by algorithms to process data from all of the above-mentioned sources to arrive at easily interpreted messages accessible to clinicians via an external programmer. Data from these sources identify lead conductor/connector interface issues and electrode/tissue interface issues indicative of lead-related mechanisms suggestive of impending or actual lead failure. The weights are "interpreted" for the user in the following manner:

- Lead-related parameters are all within range or operating normally.
- One or more of the lead parameters are out-of-range. Investigate leads.
- A number of lead parameters are out-of-range and a safety problem exists.

Messages to the User refer to three types of lead-related conditions: lead/conductor/connector messages, lead insulation messages, and biological interface messages. Examples of such messages include:

- High impedance (>4000 ohms, 2× increase over reference, among others).
- Increase in threshold(s) above preset or programmed limit.
- Reduction in R and P-wave amplitude below preset or programmed limit.

Useful, summary information from a variety of trend data are therefore presented for the use of a medical professional.

SUMMARY

A medical professional may compare the impedance value measured in an electrode-to-electrode impedance test with a known operable range or with other criteria. If the measured impedance value is within the specified criteria, e.g., the operable range, it is likely the electrode (including the lead) is functional and properly placed. If the measured impedance value is outside of the operable range, it is likely that the electrode (including the lead) is not functional, not properly placed or both. Because the operable range or other criteria for the value of electrode impedance may be known to the manufacturer of the implantable medical device, it may not be necessary in many situations to compel the medical professional to manually compare the measured impedance with the operable range.

An embodiment of the present invention uses a controller to automatically perform a comparison of electrode impedance with a known operable range and report the functional status of the electrodes (including the leads) based on that comparison. Providing a "go/no-go" indication to the user greatly simplifies the testing procedure and is significantly quicker. In addition, the actual measured impedance values may also be displayed.

A complete lead impedance test will commonly involve testing each electrode with every other electrode. This amount of information is commonly required to diagnose faults in electrode placement. The number of individual tests that must be preformed for a complete test therefore increases exponentially for every added electrode, thereby increasing the time required to run the test, which may commonly be performed in a sterile, operating room environment. An embodiment of the present invention tests the impedance of each electrode only twice, exclusively to determine if there are any faults with the electrodes. If all of the impedance measurements are within the operable range, it may be understood that the tested leads are functional and the electrodes are properly placed. Thus, any individual electrode whose impedance value test indicates that the electrode is operational need not be tested again. Remaining, non-tested electrodes may then be tested in combinations involving other non-tested electrodes and omitting tested electrodes may greatly simplify and speed the testing procedure.

Lead impedance testing is typically preformed with a physician programmer, which can be bulky and can take a considerable period of time, e.g., several minutes, to power up and become operational. In addition, it may be that the physician programmer should be operated outside of the sterile field in the operating room. An embodiment of the present invention replaces the physician programmer, for electrode testing purposes, with a light, battery powered, fast-booting, hand-held controller that powers up in a considerably shorter period of time than the physician programmer, e.g., within seconds, and that may be used within the sterile field, saving several minutes in the running of the test. In addition, because the controllers are light and simple to use, the controllers may be given to patients to perform impedance tests in their own homes.

In an embodiment, the present invention provides a controller for an implantable medical device having a plurality of electrodes, the implantable device being capable of delivering a therapeutic stimulation to a patient, having a control module, a user interface providing control of the control module by a medical professional, and an electrode interface operatively coupled between the plurality of electrodes and the control module. The control module uses the electrode interface to obtain a plurality of measurements of impedance values for a plurality of selected pairs of individual ones of the plurality of electrodes, and the user interface displays an indicia, indicative of operability of a group of at least one of the plurality of electrodes, based on a comparison of the plurality of measurements to a predetermined range, the indicia being a qualitative representation of operability of the group of at least one of the plurality of electrodes.

In an embodiment, the indicia is a first indicia, and wherein the user interface displays a second indicia upon a different result of the comparison.

In an embodiment, the user interface displays the first indicia if the comparison determines that all of the plurality of measurements of impedance values are within the predetermined range.

In an embodiment, the user interface displays a second indicia if the comparison determines that any of plurality of measurements of impedance values outside of the predetermined range.

In an embodiment, one of the plurality of electrodes is included not more than twice in the plurality of measurements of impedance values of selected ones of the plurality of electrodes.

In an embodiment, each of the plurality of electrodes is included not more than twice in the plurality of measurements of impedance values of selected ones of the plurality of electrodes.

In an embodiment, the plurality of measurements of impedance values are conducted for fewer than all of the plurality of electrodes.

In an embodiment, the plurality of measurements of impedance values are conducted only for those of the plurality of electrodes that are in use for the therapeutic stimulation.

In an embodiment, the implantable medical device further comprises a plurality of leads, each of the plurality of electrodes being associated with one of the plurality of leads, wherein each of the plurality of electrodes of each individual one of the plurality of selected pairs of electrodes are associated with the same lead, and wherein the control module uses the electrode interface to obtain a plurality of measurements of impedance values for the plurality of selected pairs.

In an embodiment, the patient has a brain having two hemispheres, each of the plurality of electrodes being associated with one of the hemispheres, wherein each of the plurality of electrodes of each of the plurality of selected pairs of electrodes are associated with the same one of the hemispheres of the brain.

In an embodiment, each individual one of the plurality of electrodes is associated with two of the plurality of selected pairs, and wherein the second indicia is displayed for an individual one of the plurality of electrodes only if each of the measurements of impedance of the plurality of selected pairs with which the individual one of the plurality of electrodes is associated are outside of the predetermined range.

In an embodiment, the present invention further provides a system capable of delivering a therapeutic stimulation to a patient, having an implantable medical device having a plurality of electrodes capable of delivering the therapeutic stimulation to the patient, and a controller, operatively coupled to the implantable medical device. The controller has a control module, a user interface providing control of the control module by a medical professional, and an electrode interface operatively coupled between the plurality of electrodes and the control module. The control module uses the electrode interface to obtain a plurality of measurements of impedance values for a plurality of selected pairs of individual ones of the plurality of electrodes, and the user interface displays an indicia, indicative of operability of a group of at least one of the plurality of electrodes, based on a comparison of the plurality of measurements to a predetermined range, the indicia being a qualitative representation of operability of the group of at least one of the plurality of electrodes.

In an embodiment, the system further comprises a remote station, the remote station being operatively coupled to the controller, the implantable medical device being operatively coupled to the remote station via far-field radio frequency communication.

In an embodiment, the remote station comprises a remote station user interface, the remote station user interface displaying the indicia to the user.

In an embodiment, the present invention further provides a method for delivering therapeutic stimulation to a patient using an implantable medical device having a plurality of electrodes. The method has the steps of obtaining a plurality of measurements of impedance values for a plurality of selected pairs of individual ones of the plurality of electrodes, and displaying an indicia based upon a result of a comparison of the plurality of measurements of impedance values with a predetermined range. The indicia is indicative of operability of a group of at least one of the plurality of electrodes, the indicia being a qualitative representation of operability of the group of at least one of the plurality of electrodes.

DRAWINGS

FIG. 3A is an illustration an external controller intended to be used in conjunction with the implantable medical device of FIG. 1;

FIG. 3B is an illustration of buttons positioned on a side of the external controller illustrated in FIG. 3A;

FIG. 3C is a screenshot of the external controller illustrated in FIG. 3A which is set to begin conducting a lead connection check;

FIG. 3D is a screenshot of the external controller illustrated in FIG. 3A having recently conducted a lead connection check;

DETAILED DESCRIPTION

The entire content of provisional U.S. Application Ser. No. 60/840,642, filed Aug. 28, 2006, and U.S. application Ser. No. 11/846,142, filed Aug. 28, 2007, is hereby incorporated by reference.

Figure 1:
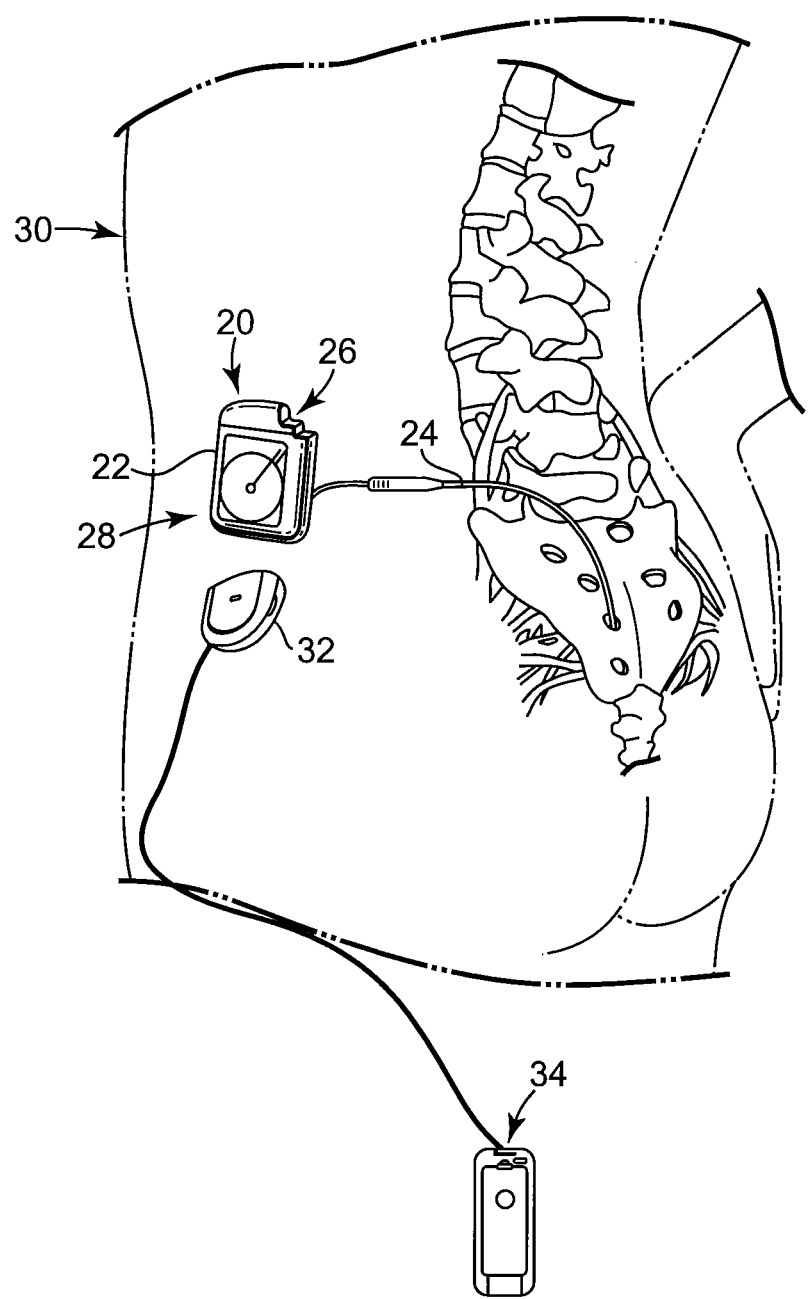
FIG. 1 illustrates an external controller used in conjunction with a implantable medical device.

FIG. 1 shows the general environment of an embodiment of implantable medical device 20. Implantable neurological stimulator 22 is shown, but other embodiments such as pacemakers and defibrillators and the like are also applicable. Implantable neurological stimulator 22 is implanted subcutaneously in side 28 of patient 30, generally at a depth of between 1.0 and 2.5 centimeters, dependent on factors such as the patient's physiology and the nature of the therapy to be delivered. Lead 24 is operatively coupled to implantable neurological stimulator 22 at header 26. Lead 24 is positioned along spinal cord 31 of patient 30. Controller 32, also called a patient programmer, may become transcutaneously coupled to implantable neurological stimulator 22 via an inductive communication link through the tissue of patient 30 through antenna 34 when antenna 34 is placed in proximity to implantable neurological stimulator 22. Though the precise maximum range for establishing an inductive communication link will vary depending on such factors as available battery power and the physical characteristics of coil 70 (FIG. 4), antenna 34 should generally be placed within six (6) centimeters of implantable medical device 22. If an inductive communication link has been established then communication may proceed until the communication is ended either by controller 32, or by breaking the communication link, commonly by increasing the distance between antenna 34 and implantable neurological stimulator 22 beyond the range at which communication may occur.

In an embodiment, controller 32 is small enough to be held comfortably in the hand of a typical adult, where it may be easily manipulated either with that hand or the user's other hand. Controller 32 may be durable enough to be sterilized and brought within a sterile field environment and durable enough to be dropped without becoming non-functional.

Figure 2:
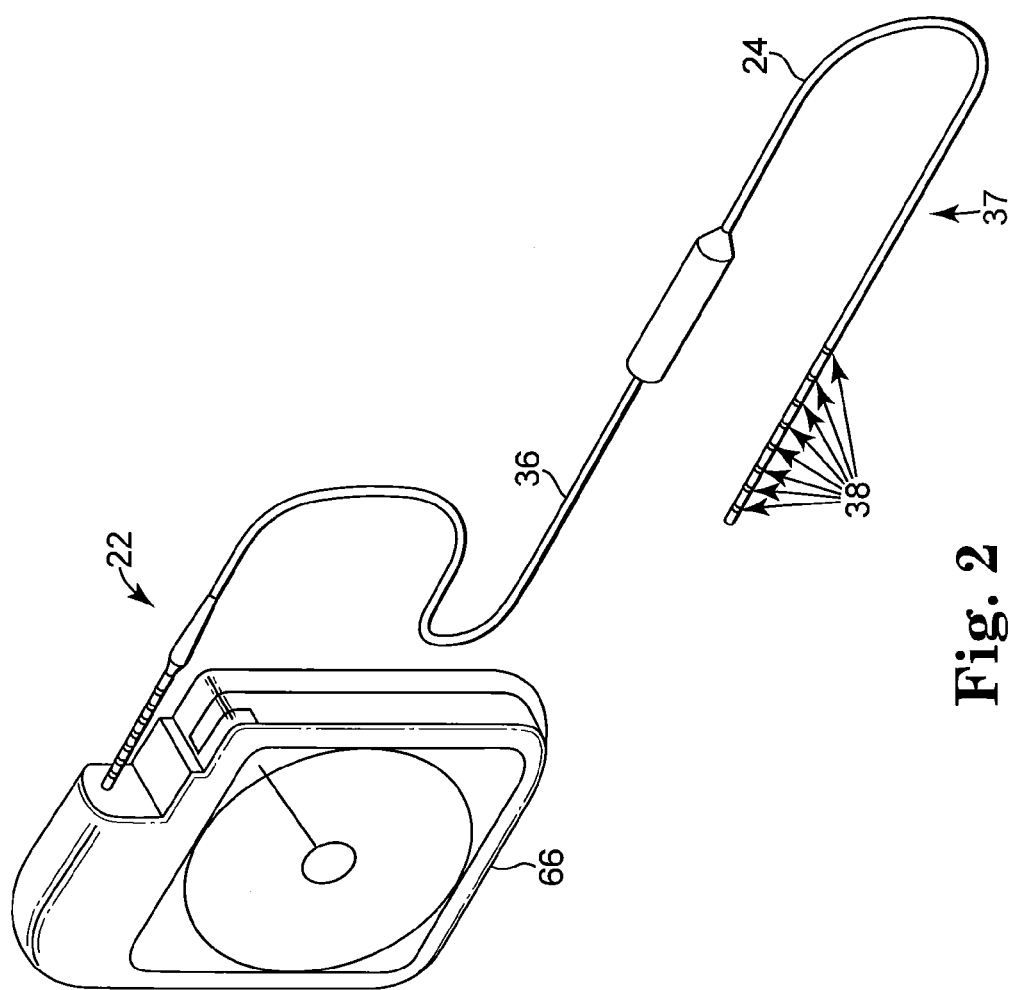
FIG. 2 illustrate the implantable medical device of FIG. 1 with associated electrodes.
Figure 4:
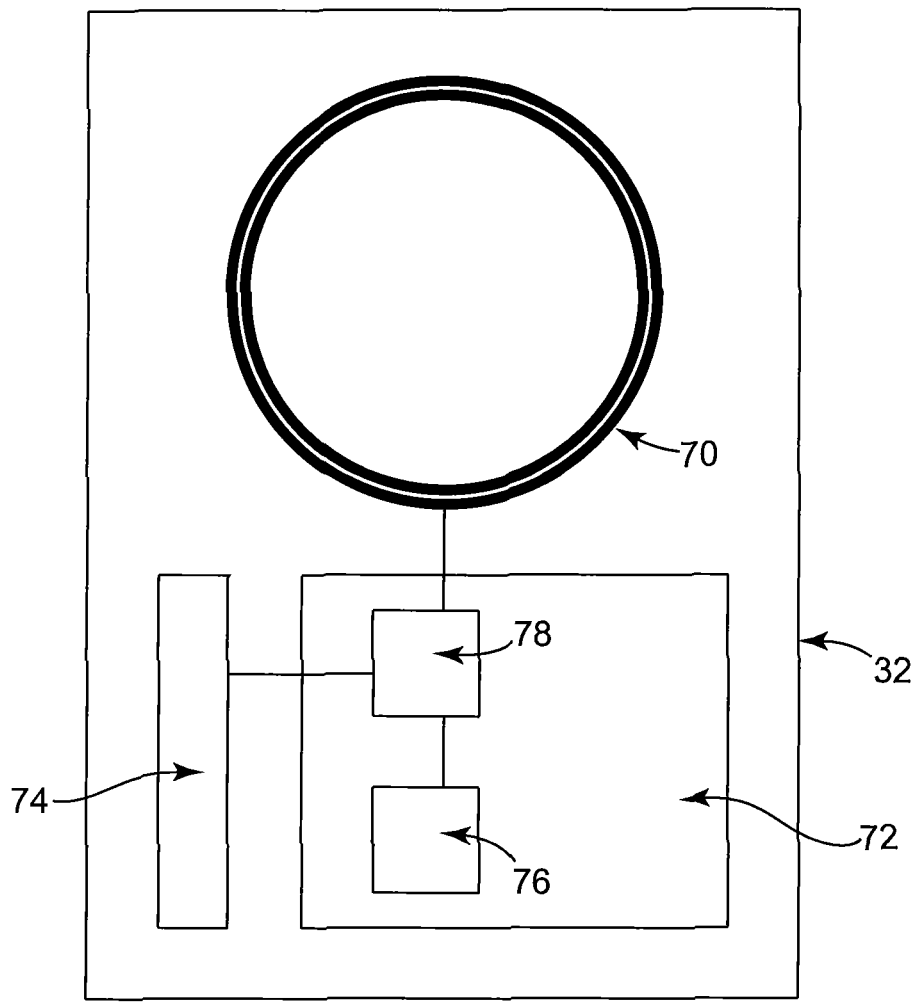
FIG. 4 is a functional block diagram of the external controller of FIG. 3.

FIG. 2 shows a closer view of implantable neurological stimulator 22 and lead 24, operatively coupled by optional extender 36. Electrodes 38 are mounted on distal end 37 of lead 24. Electrodes 38 are comprised of a conductive material, in an embodiment, metal, that come into direct contact with tissue of patient 30. Electrodes 38 are operatively coupled with implantable neurological stimulator 22 via header 26 through wires comprised of conductive material that pass through the interior of lead 24 and are operatively coupled with conductive wires in the interior of extender 36. A cutaway of implantable neurological stimulator 22 shows secondary coil 23 which may create an inductive communication link with primary coil 70 (FIG. 4).

The number of leads 24 associated with implantable neurological stimulator 22, and the number of electrodes 38 associated with each lead 24, may depend on the nature and location of the therapy implantable neurological stimulator 22 is intended to deliver. The configuration of eight electrodes 38 per lead 24 may commonly be utilized in spinal cord stimulation applications which may typically include two such eight-electrode 38 leads 24. Such a configuration may be common in applications based around the electrical stimulation of comparatively long, narrow regions of patient 30. By contrast, applications which require the stimulation of regions comparatively planar or spread out, such as deep-brain stimulation, may utilize up to four leads 24 of in four-electrode 38 per lead 24 configuration.

Commonly, each lead 24 associated with implantable neurological stimulator 22 may be identical to each other lead 24. In order to facilitate programming and testing, electrodes 38 are commonly assigned a unique alpha-numeric identifier, commonly a unique integer starting with "0" and proceeding up. In an embodiment with sixteen electrodes 38, then, each electrode 38 would be assigned an integer identifier from "0" through "15". In this embodiment, the proximal electrode 38 on one of leads 24 may be assigned the identifier "0", the next most-proximate electrode 38 "1", and so on, from proximate to distal along the lead. When all of electrodes 38 on lead 24 have been assigned an identifier, another lead 24 is selected and the proximal-to-distal assignment of identifiers continues until all electrodes 38 on all leads 24 have been assigned an identifier. In an embodiment, to further facilitate organization and testing of electrodes 38 and leads 24, electrodes 38 are then organized into groups of four electrodes 38. Electrodes 38 assigned identifiers "0" through "3" would be assigned to a first group, electrodes 38 assigned identifiers "4" through "7" would be assigned to a second group, and so on until all electrodes 38 have been assigned to a group. In an embodiment, four groups may be created.

Additionally, embodiments of the present invention are envisioned for applications that substitute other types of implantable medical devices for implantable neurological stimulator 22, such as pacemakers and defibrillators. In these embodiments, leads 24 may be of significantly different configuration from those utilized by implantable neurological stimulator 22. In an embodiment utilizing an implantable defibrillator, leads may include pacing leads 24 with a pair of pacing electrodes 38 as well as defibrillation leads 24, potentially including both defibrillation and pacing electrodes 38.

FIG. 3A shows controller 32. Display 52 displays both text and graphical presentations of data and menus to a user to allow the user to control, in some respects, implantable neurological stimulator 22, and to obtain various types of information from implantable neurological stimulator 22. Buttons 54 may provide the primary interface for the user to control the functionality of controller 32 and implantable medical device 22. In various embodiments the number, positioning and nature of buttons 54 differs dependent on the nature of implantable medical device 22 and the therapy implantable medical device 22 is configured to deliver. For example, in the embodiment depicted in FIG. 3A, primarily utilized for deep brain stimulation, it may be undesirable to allow a user very much control over the functionality of implantable medical device 22. Because the user is given relatively little means for impacting implantable medical device 22 performance, there may be relatively little need for many interface buttons 54. Thus, buttons 54 are limited only to two at the top of the screen, utilized for accessing functions, and the four arrow buttons 54 at the bottom of controller 32, used for scrolling among menus, as well as a power button.

By contrast, in an embodiment depicted in FIG. 3B, in some applications it may be desirable for the user to exert more control over the function of implantable neurological stimulator 22, and thus buttons 54 on the side of controller 32 are provided. An example of such a situation where increased user control may include spinal stimulation, as illustrated in FIG. 1. The extra buttons 54 may allow a user added control over the amount of electrical stimulation delivered by implantable neurological stimulator 22.

FIG. 3C depicts a screenshot 55 of controller 32 to begin conducting a Lead Connection Check, or "LCC". In an embodiment, the screen 55 may be arrived at by pressing and holding both top buttons 54 for three seconds. Once screen 55 is arrived at, the user may commence the LCC by pressing one or more of buttons 54, depending on the various embodiments of controller 32. In an embodiment, graphic 57 on display 52 indicates to the user which button to press. In an embodiment illustrated in FIG. 3C graphic 57 indicates that the user should press the sync button (see FIG. 3B) in order to commence the LCC.

FIG. 3D depicts a screenshot 59 of the results display from a recently conducted LCC. In the illustrated embodiment, the display identifies that the LCC test had just occurred, as well as a qualitative indication of the result of the LCC, in this case illustrated as a textual indicia of the number of electrodes 38 that had passed the test (see FIG. 5). In alternative embodiments, results may report the number of electrodes that failed to pass, or may provide graphical indicia of the result of the LCC test. Such graphical indicia may include a mark corresponding to each electrode, the mark indicating either a pass or a fail, or charts, such as a pie chart or a bar with a length corresponding to the number of electrodes 38 that had passed the test.

In an embodiment, a characteristic of the above described embodiment is the distinction these embodiments make between indicia that indicate a qualitative result, rather than indicating a quantitative result corresponding to the actual measure of impedance between each pair of electrodes 38. The above-described embodiments provide the advantage of a simple to understand result, compared with a quantitative result that must be interpreted against the predetermined range for passage of the various impedance tests. A qualitative representation provides a diagnostic tool that may suffice in all but the most complicated of diagnostic situations, such as situations in which a user is attempting to characterize and understand a major fault in the system. However, as reliability in electrodes 38 and leads 24 tends to be very high, a simple qualitative representation may, in the overwhelming majority of situations in which there is no issue with electrodes 38 or leads 24, provide the best and most useful data to a user, indicating either that everything is OK, or that there may be issues that need to be followed up on with a quantitative diagnostic with quantitative representations.

In the case of the embodiment depicted in FIG. 3D, the qualitative representation is a binary representation, as it simply shows the number of electrodes 38 that are "OK", with the remainder of electrodes 38 not indicated as being "OK" being bad. Various contemplated embodiments flip the binary representations, with "bad" being displayed on display 52 along with the number of "bad" electrodes. Additionally, alternative, largely-synonymous terminology is also contemplated, for instance substituting "good" or "functional" for "OK". Further embodiments utilizing trinary qualitative representations are likewise contemplated, which may, for instance, include FIG. 4 depicts a block diagram of controller 32. Primary coil 70 enables controller 32 to establish an inductive communication link with implantable neurological stimulator 22 via secondary coil 23 when primary coil 70 is placed in proximity of secondary coil 23 (in an embodiment, within 6.0 centimeters). Battery 74 provides direct current power to electronics 72. In various embodiments, battery 74 may be rechargeable or disposable, as batteries may improve patient safety by foreclosing the possibility of electrical failure creating an open circuit between patient 30 and a wall outlet. Alternatively, battery 74 may be substituted with power supplied by an outside source, either including a power converter as a component of controller 32, allowing controller 32 to run off of AC power directly from a standard outlet, or an embodiment may require input power be converted to suitable properties prior to arriving at controller 32.

Controller 32 additionally includes various electronics 72. Electronics 72 include various modules, including control module 76 which, in an embodiment, comprises, at least in part, off-the-shelf hardware components such as a processor and a memory module, as well as custom-designed componentry used in controlling the various components of controller 32, as well as conducting electrode impedance tests. Interface module 78 may be operatively coupled to coil 70 and control module 76 and include componentry for sending and receiving information via coil 70, including transmit and receive circuits known in the art. Electronics 72 are likewise operatively coupled to battery 74, display 52 and input buttons 54.

Figure 5:
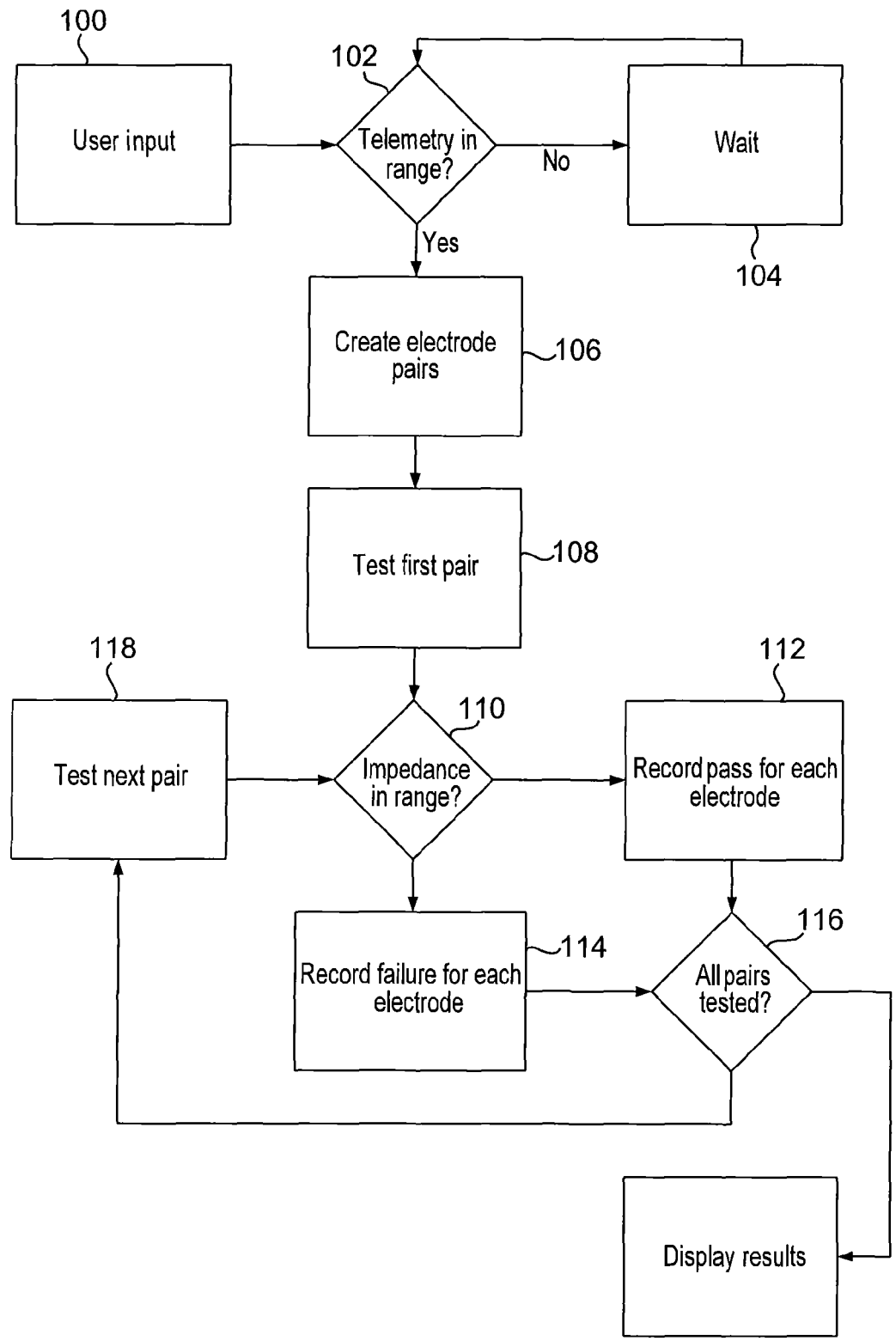
FIG. 5 is a flow chart illustrating function of an embodiment of the present invention.

FIG. 5 shows a flowchart depicting the function of controller 32. When a medical professional commences (100) a lead impedance test via input buttons 54, control module 76 determines if an inductive link has been established (102) between coil 70 and implantable neurological stimulator 24. If an inductive link has not been established, control module 76 may wait (104) and periodically check if an inductive link has been established (102), repeating as necessary until a timeout condition occurs.

If an inductive link has been established, control module establishes (106) pairs of electrodes 38 that will be tested for impedance. Electrode 38 pairs may be created utilizing a variety of different methods, depending on the particular circumstances of the test. In an embodiment, each subject electrode 38 is included in a total of two pairs, with the other electrode in each pair being selected from any of the other electrodes 38 assigned to the same group of four as subject electrode 38 (see FIG. 2). In this embodiment, electrodes 38 are paired with electrodes 38 with adjacent identifier numbers, or, if electrode 38 is either the first or the last electrode 38 in a group, with the electrode 38 in the group that is adjacent as well as the other end electrode 38 in the group. In this embodiment, electrodes 38 are paired with only two other electrodes 38. In an alternative embodiment, each electrode 38 is paired with each other electrode 38 in its group.

The above described embodiment avoids potential issues commonly encountered in electrode impedance testing. In addition to simplifying the selection of electrode pairs, the grouping of electrodes automatically avoids certain potential hazards, such as testing for impedance between electrodes that are on opposite sides of a patient's 30 brain, in an embodiment where implantable neurological stimulator is substituted for a deep brain stimulator. The above embodiment likewise helps with patient safety and comfort by ensuring that electrodes 38 that are tested as pairs are in close proximity of each other, thereby preventing long current paths over potentially sensitive area's of patient's 30 body.

Further, by only testing each electrode 38 twice, the above-described embodiments tend to reduce test time compared with impedance tests that test each electrode 38 with every other electrode 38. These embodiments also tend to save on battery 74 power by reducing the amount of energy used to conduct the impedance testing. However, in spite of the savings of time and energy, these embodiments do not lead to any reduced accuracy in determining basic qualitative function of electrodes 38. Because each electrode 38 is tested against two other electrodes 38

Further embodiments are envisioned where each electrode is tested only once, thereby further reducing the amount of time to conduct testing due to approximately halving the number of impedance tests conducted, as well as reducing and the amount of energy consumed. The information derived from such testing, however, may only be precise to indicate a failure in at least one of the two electrodes 38 tested, rather than a failure in a particular electrode 38. However, in situations where a user is only concerned with whether the system as a whole may be experiencing any failures, rather than which, if any, individual electrodes 38 are experiencing failures, the decrease in precise qualitative information may be irrelevant, while still yielding the benefit of reduced test time and reduced energy consumption.

After the electrode pairs have been selected, the first such pair is tested (108). Using Ohm's Law, control module 76 determines if the impedance between the electrode 38 pair is within (110) the predetermined allowable range by placing a voltage, or sending a current down, one of the electrodes 38 of the pair, measuring the voltage or current on the other electrode of the pair, and then utilizing Ohm's Law to determine the impedance. If the measured impedance is within (110) a predetermined range then controller 32 records (112) a note indicating that the electrode pair passed. If the measured impedance is outside of the predetermined range then controller 32 records (114) a note that the electrode pair failed. In an embodiment, controller 32 records results from steps (112) and (114) in a memory module in electronics 72. If all electrode pairs have not yet been tested (116) the next electrode pair is then tested (118).

If all electrode pairs have been tested then controller 32 determines and displays (118) the results. Results are determined by checking the results for each electrode 38. In an embodiment, for each electrode that was part of one or no electrode pairs 38 that failed (114), a counter is incremented by one. For each electrode 38 that has two failures, the counter is not incremented. After all electrodes 38 have been accounted for, the value of the counter, which indicates the number of electrodes that have passed, may be displayed on display 52, along with an indication that the number represents the number of electrodes 38 that have passed the impedance test.

Alternate embodiments could display the actual impedance value with the user scrolling the list of measurements, and use a variety of upper and lower limits for advanced troubleshooting, e.g., greater than 3,600 ohms, greater than 5,000 ohms or greater than 10,000 ohms. However, as controller 32 may primarily be designed to be used in preliminary testing to either verify that all electrodes 38 are operable and adequately positioned, or to detect the existence of a fault condition, such an alternate embodiment may not commonly be available to a user.

Thus, embodiments of the controller for obtaining prescriptive analysis of functionality of implantable medical device leads, system and method therefore are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A controller for an implantable medical device having a plurality of electrodes, said implantable device being capable of delivering a therapeutic stimulation to a patient, comprising:
a control module;
a user interface providing control of said control module by a medical professional;

an electrode interface operatively coupled between said plurality of electrodes and said control module;

wherein each of said plurality of electrodes are coupled with another one of said plurality of electrodes to form a plurality of electrode pairs;

wherein said control module is configured to select a portion of said plurality of electrode pairs forming a plurality of groups of electrode pairs, each of said plurality of groups of electrode pairs having fewer than all of said plurality of electrode pairs;

wherein said control module is further configured to select one of said plurality of groups of electrode pairs;

wherein said control module is further configured to use said electrode interface to obtain measurements of impedance values for each of electrode pairs in said one of said plurality of groups of electrode pairs; and wherein said user interface displays an indicia, indicative of operability of said electrode pairs in said one of said group of plurality of electrode pairs, based on a comparison of said plurality of measurements to a predetermined range, said indicia being a qualitative representation of operability of said electrode pairs in said one of said group of electrode pairs.

2. A controller as in claim 1 wherein said indicia is a first indicia, and wherein said user interface displays a second indicia upon a different result of said comparison.

3. A controller as in claim 2 wherein said user interface displays said first indicia if said comparison determines that all of said plurality of measurements of impedance values are within said predetermined range.

4. A controller as in claim 3 wherein said user interface displays a second indicia if said comparison determines that any of plurality of measurements of impedance values are outside of said predetermined range.

5. A controller as in claim 2 wherein said controller associates each individual one of said plurality of electrode pairs with two of said plurality of groups of electrode pairs, and wherein said second indicia is displayed for an individual one of said plurality of electrodes only if each of said measurements of impedance of said plurality of electrode pairs with which said individual one of said plurality of electrode pairs is associated are outside of said predetermined range.

6. A controller as in claim 1 wherein said controller includes one of said plurality of electrode pairs not more than twice in said plurality of measurements of impedance values of said plurality of electrode pairs.

7. A controller as in claim 1 wherein said controller conducts said plurality of measurements of impedance values for fewer than all of said plurality of groups of electrode pairs.

8. A controller as in claim 7 wherein said controller conducts said plurality of measurements of impedance values only for those of said plurality of groups of electrode pairs that are in use for said therapeutic stimulation.

9. A controller as in claim 1 wherein said patient has a brain having two hemispheres, each of said plurality of groups of electrode pairs being associated with one of said hemispheres, wherein each of said electrode pairs in said plurality of groups of electrode pairs are associated with a same one of said hemispheres of said brain.

10. A controller as in claim 1 wherein said qualitative representation is a binary qualitative representation.

11. A system capable of delivering a therapeutic stimulation to a patient, comprising:

an implantable medical device having a plurality of electrodes capable of delivering said therapeutic stimulation to said patient; and a controller, operatively coupled to said implantable medical device, comprising: a control module; a user interface providing control of said control module by a medical professional; an electrode interface operatively coupled between said plurality of electrodes and said control module;

wherein each of said plurality of electrodes are coupled with another one of said plurality of electrodes to form a plurality of electrode pairs;

wherein said control module is configured to select a portion of said plurality of electrode pairs forming a plurality of groups of electrode pairs, each of said plurality of groups of electrode pairs having fewer than all of said plurality of electrode pairs;

wherein said control module is further configured to select one of said plurality of groups of electrode pairs;

wherein said control module is further configured to use said electrode interface to obtain measurements of impedance values for each of said electrode pairs in said one of said plurality of groups of electrode pairs; and wherein said user interface displays an indicia, indicative of operability of said electrode pairs in said one of said group of electrode pairs, based on a comparison of said plurality of measurements to a predetermined range, said indicia being a qualitative representation of operability of said electrode pairs in said one of said plurality of electrode pairs.

12. A method for delivering therapeutic stimulation to a patient using an implantable medical device having a plurality of electrodes, comprising the steps of:

coupling said plurality of electrodes into a plurality of electrode pairs;

obtaining a plurality of measurements of impedance values for a plurality of said electrode pairs from one of a plurality of groups of electrode pairs, each of said plurality of groups of electrode pairs having fewer than all of said electrode pairs; and displaying an indicia, indicative of operability of each of said electrode pairs in one of said plurality of groups of electrode pairs, based on a comparison of said plurality of measurements to a predetermined range, said indicia being a qualitative representation of operability of said electrode pairs in said one of said plurality of groups of electrode pairs.

13. A method as in claim 12 wherein said indicia is a first indicia, further comprising the step of displaying a second indicia upon a different result of said comparison.

14. A method as in claim 12 wherein said displaying step displays said first indicia if said comparison determines that all of said plurality of measurements of impedance values are within said predetermined range.

15. A method as in claim 12 wherein said displaying step displays a second indicia if said comparison determines that any of plurality of measurements of impedance values are outside of said predetermined range.

16. A method as in claim 15 wherein said first indicia represents an operable state and wherein said second indicia represents a non-operable state.

17. A method as in claim 12 wherein said obtaining step obtains one of said plurality of measurements of impedance values for one of said selected pairs of electrodes only once.

18. A method as in claim 12 wherein said obtaining step obtains said plurality of measurements of impedance values for fewer than all of said plurality of groups of electrode pairs.

19. A method as in claim 18 wherein said obtaining step obtains said plurality of measurements of impedance values only for those of said plurality of groups of electrode pairs that are in use for said therapeutic stimulation.

20. A method as in claim 12 wherein said patient has a brain having two hemispheres, each of said plurality of groups of electrode pairs being associated with one of said hemispheres, wherein each of said electrode pairs of each of said plurality of groups of electrode pairs are associated with a same one of said hemispheres of said brain.

21. A method as in claim 20, wherein each individual one of said plurality of electrode pairs is associated with two of said plurality of groups of electrode pairs, and wherein said displaying step displays said second indicia for an individual one of said plurality of electrodes only if each of said measurements of impedance of said plurality of pairs with which said individual one of said plurality of groups of electrode pairs is associated are outside of said predetermined range.

22. A method as in claim 12 wherein said first indicia is based on a number of measured impedance values measured either within or outside of said predetermined range.

\* \* \* \* \*